(12) United States Patent
Clare et al.

(10) Patent No.: US 9,877,887 B2
(45) Date of Patent: Jan. 30, 2018

(54) COMPRESSION THERAPY APPARATUS, SYSTEMS, AND METHODS

(71) Applicant: KCI Licensing, Inc., San Antonio, TX (US)

(72) Inventors: Rob Clare, Bournemouth (GB); Elliott Rider, Acklam (GB)

(73) Assignee: KCI Licensing, Inc., San Antonio, TX (US)

(*) Notice: Subject to any disclaimer, the term of this patent is extended or adjusted under 35 U.S.C. 154(b) by 397 days.

(21) Appl. No.: 14/206,396

(22) Filed: Mar. 12, 2014

(65) Prior Publication Data

US 2014/0276274 A1 Sep. 18, 2014

Related U.S. Application Data

(60) Provisional application No. 61/784,655, filed on Mar. 14, 2013.

(51) Int. Cl.
*A61F 13/00* (2006.01)
*A61H 1/00* (2006.01)
*A61F 13/06* (2006.01)

(52) U.S. Cl.
CPC ............ *A61H 1/008* (2013.01); *A61F 13/064* (2013.01); *Y10T 29/49826* (2015.01)

(58) Field of Classification Search
CPC ............ A61H 1/008; A61H 2201/0207; A61H 2201/0228; A61H 2201/1207; A61H 2201/1635; A61H 2201/164; A61H 2201/165; A61H 2201/169; A61H 2201/1697; A61H 2201/50; A61H 2201/501; A61H 2201/5015; A61H 3/00; A61H 2201/5097; A61H 1/024; A61H 1/0244; A61H 1/0266; A61H 2201/1215;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

International Search Report and Written Opinion for corresponding PCT/US2014/024845, dated Nov. 6, 2014.
(Continued)

*Primary Examiner* — Kim M Lewis

(57) ABSTRACT

A compression therapy apparatus for applying therapeutic compression to a limb includes a bandage having a trunk, a first end, a second end, and a compression line between the first end and the second end. The apparatus also includes a plurality of compression control members disposed on the trunk along the compression line. Each compression control member defines a compression zone and is adapted to independently control a therapeutic compression associated with the compression zone. The plurality of compression control members are configured to provide a substantially continuous compression profile along the compression line.

29 Claims, 7 Drawing Sheets

(58) Field of Classification Search
CPC .... A61H 2201/1238; A61H 2201/1246; A61H 2201/1652; A61H 2201/1664; A61H 1/006; A61F 13/08; A61F 13/085; A61F 13/06; A61F 13/064; A61F 5/0111; A61F 5/0113; A61F 5/0127
USPC .................................. 602/16, 20–28, 60–64
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,856,008 A * | 12/1974 | Fowler | A61F 13/085 128/DIG. 15 |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,020,164 A * | 6/1991 | Edwards | A41B 11/00 2/239 |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 6,827,653 B2 * | 12/2004 | Be | A63B 71/148 2/161.1 |
| 6,974,433 B2 | 12/2005 | Hess | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2006/0079852 A1 | 4/2006 | Bubb et al. | |
| 2006/0156517 A1 | 7/2006 | Hammerslag et al. | |
| 2007/0169378 A1 | 7/2007 | Sodeberg et al. | |
| 2008/0060167 A1 | 3/2008 | Hammerslag et al. | |
| 2008/0060168 A1 | 3/2008 | Hammerslag et al. | |
| 2008/0066272 A1 | 3/2008 | Hammerslag et al. | |
| 2008/0066345 A1 | 3/2008 | Hammerslag et al. | |
| 2008/0066346 A1 | 3/2008 | Hammerslag et al. | |
| 2008/0083135 A1 | 4/2008 | Hammerslag et al. | |
| 2010/0168636 A1 | 7/2010 | Allard | |
| 2011/0144554 A1 | 6/2011 | Weaver, II et al. | |
| 2011/0197362 A1 * | 8/2011 | Chella | A61F 5/0111 5/650 |
| 2012/0029404 A1 * | 2/2012 | Weaver, II | A61F 5/0111 602/27 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |

(56) References Cited

FOREIGN PATENT DOCUMENTS

| | | |
|---|---|---|
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

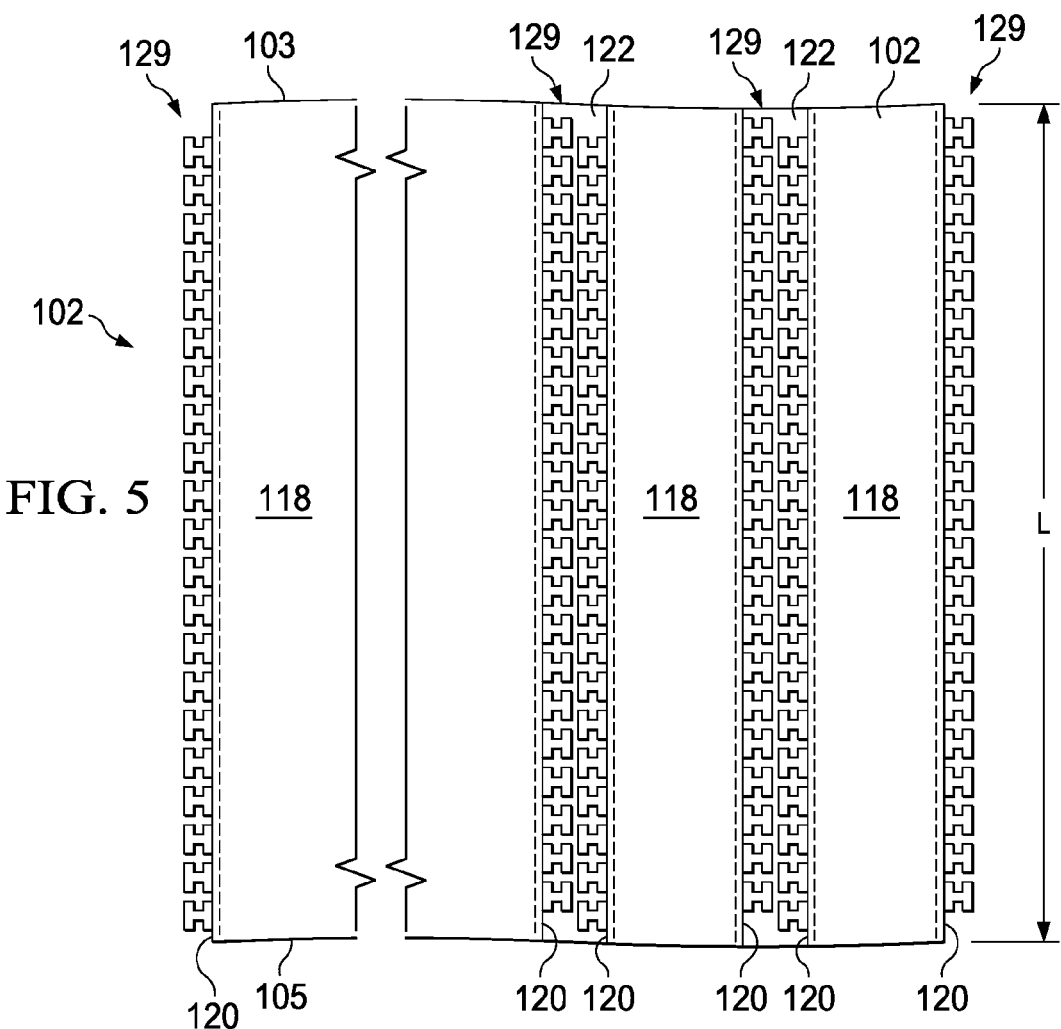
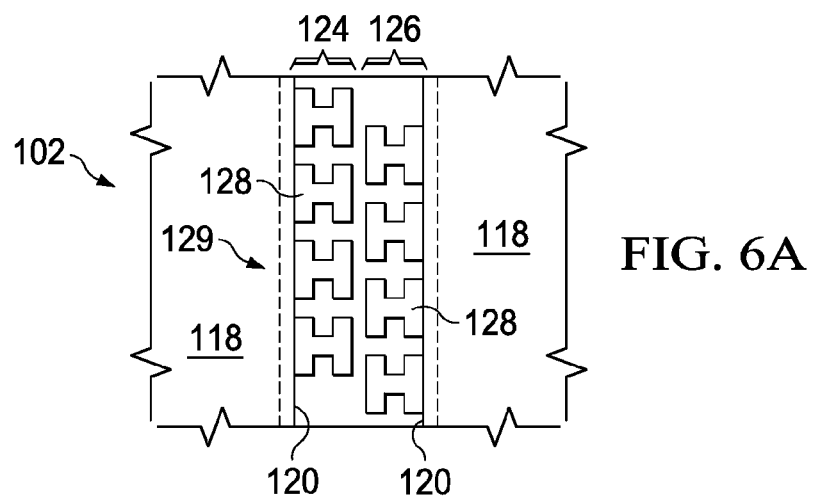

US 9,877,887 B2

COMPRESSION THERAPY APPARATUS, SYSTEMS, AND METHODS

Under 35 U.S.C. § 119(e), this application claims priority to and the benefit of U.S. Provisional Patent Application No. 61/784,655 filed Mar. 14, 2013, entitled "Compression Therapy Apparatus, System, and Method," the disclosure of which is hereby incorporated by reference in its entirety.

TECHNICAL FIELD

The present disclosure relates generally to compression therapy and, more particularly, but not by way of limitation, to compression therapy apparatuses and systems having an adjustable compression profile and methods for making and using the same.

BACKGROUND

Many people suffer from venous diseases, which are conditions related to veins that become diseased or abnormal. For example, vein walls may become weak or damaged, causing the blood to flow backward when muscles surrounding the veins relax. Backwards flow of blood may cause high pressure in the veins, resulting in stretching, twisting, and swelling of veins. Venous disease may include spider veins, varicose veins, leg swelling and leg pain, chronic venous insufficiency, leg epidermis changes, leg ulcers, phlebitis, vascular malformations, and venous malformations, for example. Mild venous disease does not typically affect the day to day life of a person suffering from venous disease; however, severe cases can be debilitating.

To facilitate healing of venous disease, a firm-fitting wrap or elastic bandage may be used to apply compression to a limb or other tissue site. However, the bandage may be uncomfortable, may apply compression in a non-uniform manner, and may be difficult to take off and put on, causing many patients to discontinue treatment prior to healing of the venous disease.

SUMMARY

According to some exemplary embodiments, a compression therapy apparatus may include a bandage having a trunk, a first end, a second end, and a compression line between the first end and the second end. The compression therapy apparatus also may include a plurality of compression control members disposed on the trunk along the compression line. Each compression control member defines a compression zone and may be adapted to independently control a therapeutic compression associated with the compression zone. The plurality of compression control members are configured to provide a substantially continuous compression profile along the compression line.

According to other exemplary embodiments, a compression therapy apparatus may include a bandage having a first end, a second end, a trunk extending from the first end to the second end, and opposing edges extending from the first end to the second end. The compression therapy apparatus also may include at least one pair of opposing clip mechanisms coupled to the bandage adjacent the opposing edges along the trunk of the bandage and operable to adjust the circumference of the bandage. The compression therapy apparatus also may include a compression control member coupled to the bandage and configured to exert a force on the bandage to provide therapeutic compression to the trunk in a compression zone.

According to yet other exemplary embodiments, a method for providing compression therapy to a tissue site may provide a bandage having a trunk, a first end, a second end, and a compression line between the first end and the second end. The bandage also may include a plurality of compression control members disposed on the trunk along the compression line. Each compression control member can define a compression zone and may be adapted to independently control a therapeutic compression associated with the compression zone. The plurality of compression control members may be configured to provide a substantially continuous compression profile along the compression line. A size of the tissue site can be determined, the bandage can be sized to accommodate the tissue site, and the tissue site can be inserted into an aperture of the bandage. The compression control member can be operated to apply therapeutic compression.

According to still other embodiments, a method of manufacturing a compression therapy apparatus may be disclosed. A bandage having a trunk, a first end, a second end, and a compression line between the first end and the second end may be provided. A plurality of compression control members on the trunk can be coupled along the compression line. Each compression control member can define a compression zone and may be adapted to independently control a therapeutic compression associated with the compression zone. The plurality of compression control members can be configured to provide a substantially continuous compression profile along the compression line.

Other aspects, features, and advantages of the exemplary embodiments will become apparent with reference to the drawings and detailed description that follow.

BRIEF DESCRIPTION OF THE DRAWINGS

FIG. 5 is a partial rear view of the therapy system of FIG. 1, illustrating an example embodiment of a clip mechanism;

FIG. 6A is a detail view of the clip mechanism of FIG. 5 in an unfastened configuration;

DETAILED DESCRIPTION OF EXEMPLARY EMBODIMENTS

New and useful systems, methods, and apparatuses for providing compression therapy to a tissue site are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

Spatial relationships between various elements or spatial orientation of various elements may be described or depicted in the attached drawings. In general, such relationships or orientations assume a frame of reference consistent with or relative to a patient in a position to receive compression therapy. However, as should be recognized by those skilled in the art, this frame of reference is merely a descriptive expedient rather than a strict prescription.

Figure 1:
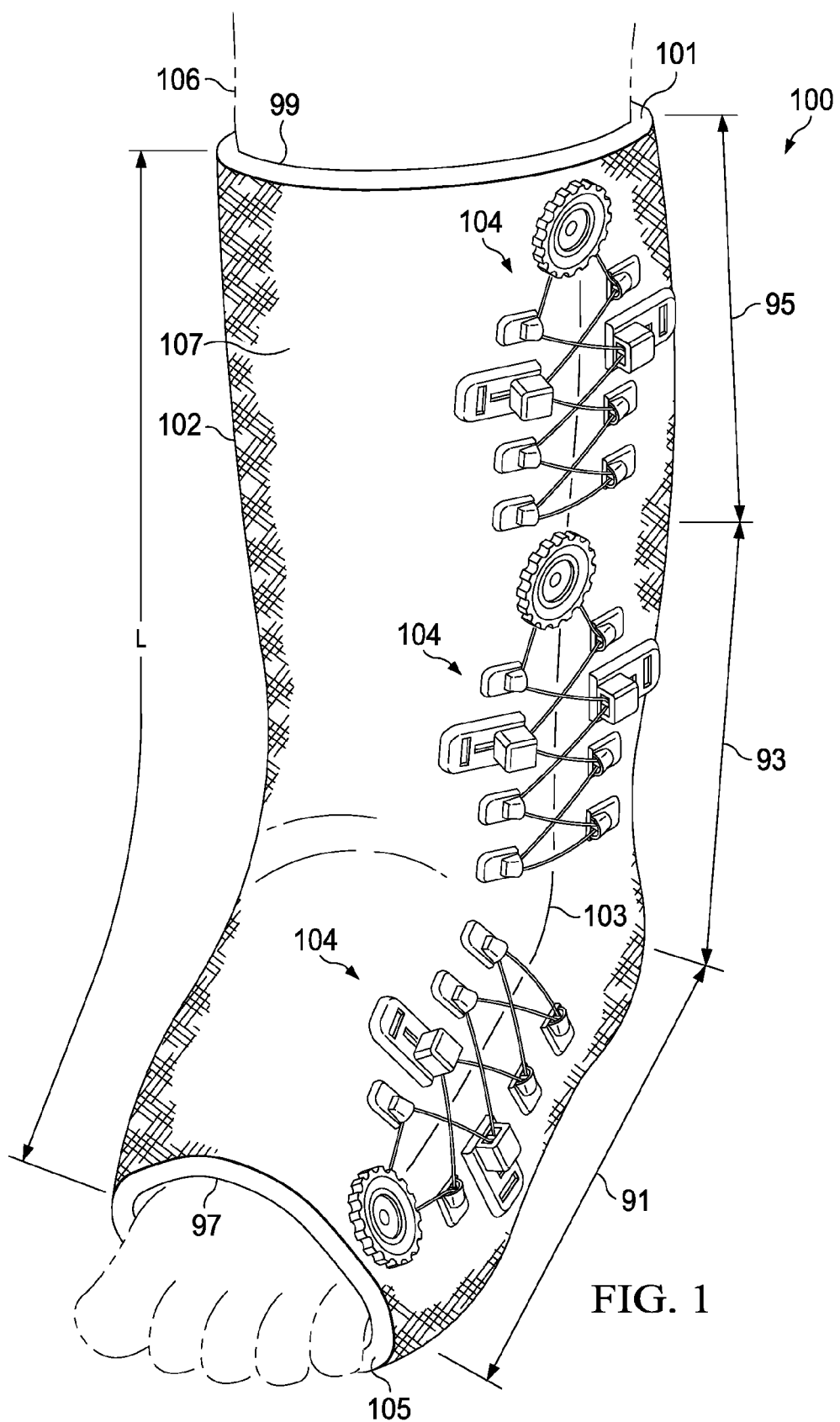
FIG. 1 is a perspective view of an illustrative therapy system for treating a tissue site.

FIG. 1 is a perspective view of an exemplary embodiment of a therapy system 100 that can provide therapeutic compression of a tissue site in accordance with this specification. As illustrated, the therapy system 100 may include a form-fitting bandage, such as a bandage 102 and one or more compression control members, such as compression control members 104.

The example embodiment of the bandage 102 illustrated in FIG. 1 generally has a first end 101, a second end 105, and a trunk 107 interposed between the first end 101 and the second end 105. In some embodiments, the bandage 102 may be adapted to receive a tissue site, such as a limb. As illustrated in FIG. 1, for example, the first end 101 may include an aperture 99 sized to receive a limb, and the bandage 102 may be adapted to cover the limb. For example, a leg 106 may be inserted through the aperture 99 so that an interior surface of the bandage 102 may be in contact with an epidermis of the portion of the leg 106 that is adjacent to the bandage 102. The second end 105 may also include an aperture 97 adapted to allow a portion of the leg 106 to protrude through the bandage 102, which may provide additional comfort or other benefit in some applications.

The bandage 102 generally represents any type of bandage, stocking, wrap, or other garment suitable for contact with a tissue site. Generally, the bandage 102 may be formed of an elastic material adapted to conform to a limb and exert pressure on a tissue site. In exemplary embodiments, the bandage 102 may be formed of a neoprene material. The bandage 102 may be formed of other materials that may be comfortable in contact with a tissue site or epidermis surrounding a tissue site and may not stretch significantly. In other exemplary embodiments, the bandage 102 may be provided in multiple sizes to fit varying leg sizes.

The bandage 102 may be particularly beneficial for treating venous disease, such as leg ulcers or oedema, which are often treated with compression therapy. Compression of a leg, for example, may increase the pressure within veins of the leg and, particularly the veins proximate to a surface of the leg. Veins proximate to a surface of a leg may also be known as superficial veins. Compression generally encourages blood flow from superficial veins toward deeper veins where blood may be more readily carried out of a leg. An increase in pressure in veins can decrease swelling and can reduce symptoms of venous leg disease.

However, therapeutic compression can be difficult to apply, and may require different compression on different portions of a limb. The variation of compression on a limb or other tissue site to encourage blood flow in a desired direction is generally referred to herein as a "compression profile." For example, a compression profile may be prescribed to encourage blood flow from an ankle to a thigh of a leg. Compression is usually graduated with the highest pressure at an ankle and the lowest pressure at higher parts of a leg proximate to a knee or pelvis.

Successful application of a prescribed compression profile to a limb or other tissue site with a conventional compression bandage is highly dependent on the experience of a treating clinician. For example, pressure beneath a compression bandage on a limb is dependent on the bandage tension, limb circumference, bandage width, and the number of layers of the bandage. Moreover, a compression bandage must be held in tension when applying the compression bandage. It can be difficult to maintain the appropriate tension on a compression bandage to achieve the correct compression profile on a limb while wrapping the compression bandage around the limb.

Compression therapy is also dependent on patient compliance. A majority of patients receiving compression therapy can reside in their home, and patients are often not monitored closely for compliance with compression therapy. Many patients remove compression bandages due to discomfort caused by compression therapy. Other patients may remove compression bandages to put on footwear. However, the complexity of applying a conventional compression bandage usually prevents successful application of the compression bandage by a patient. Once a patient removes a compression bandage, the patient may be unable to properly receive compression therapy until a clinician or other trained provider is available to reapply the compression bandage. Consequently, a venous leg condition that may be benefitted by proper compression therapy may worsen.

As disclosed herein, the therapy system 100 can overcome these shortcomings and others by providing a bandage having compression control members that facilitate application of a prescribed compression profile. In some exemplary embodiments the bandage 102 may be divided into compression zones. For example, in the embodiment illustrated in FIG. 1, the bandage 102 is divided into a first compression zone 95 adapted to be positioned over a calf of the leg 106, a second compression zone 93 adapted to be positioned over an ankle of the leg 106, and a third compression zone 91 adapted to be positioned over a portion of a foot of the leg 106. Moreover, as illustrated in FIG. 1, a compression control member 104 can be disposed on an exterior surface of the trunk 107 in each of the compression zones to provide localized control of compression applied in the zone. Thus, stated differently, the portion of the bandage 102 to which each compression control member 104 applies compression may be referred to as a compression zone. Each compression zone 95, 93, 91 may extend circumferentially around the bandage 102 and along a portion of a compression line 103 that extends beyond the physical boundary of the compression control members 104. Consequently, the compression zones may be discrete or may overlap in some embodiments. Each compression control member 104 may also provide uniform compression in a compression zone 95, 93, 91. For example, the control member 104 disposed on the trunk 107 in the first compression zone 95 may provide the substantially same amount of compression proximate to the first end 101 of the bandage 102 as the amount of compression provided proximate to the boundary of the first compression zone 95 and the second compression zone 93.

In some exemplary embodiments, the compression line 103 may be a cut, area of weakening, or flexible portion of the bandage 102 configured to allow movement of the bandage 102 in a circumferential direction. For example, the bandage 102 may increase or decrease in circumference. In other exemplary embodiments, the compression line 103 may be a seam joining two ends of the trunk 107. In still other embodiments, the compression line 103 may be a line of orientation for identification of the components of the therapy system 100. In some exemplary embodiments, the compression line 103 may extend a portion of a length L of the bandage 102. In other exemplary embodiments, the compression line 103 may extend an entirety of the length L of the bandage 102.

The compression control members 104 may generally be disposed on and coupled to the exterior surface of the trunk 107. In general, components of the therapy system 100 may be coupled directly or indirectly. For example, the compression control members 104 may be coupled directly to the bandage 102 and be indirectly coupled to the leg 106 through the bandage 102. In some embodiments, the compression control members 104 may be contiguously disposed along the compression line 103. In some embodiments, the compression control members 104 may be disposed on the trunk 107 so that the compression line 103 substantially bisects each compression control member 104. In other embodiments, the compression control members 104 may be disposed on the trunk 107 so that the compression line 103 does not bisect each compression control member 104.

Figure 2A:
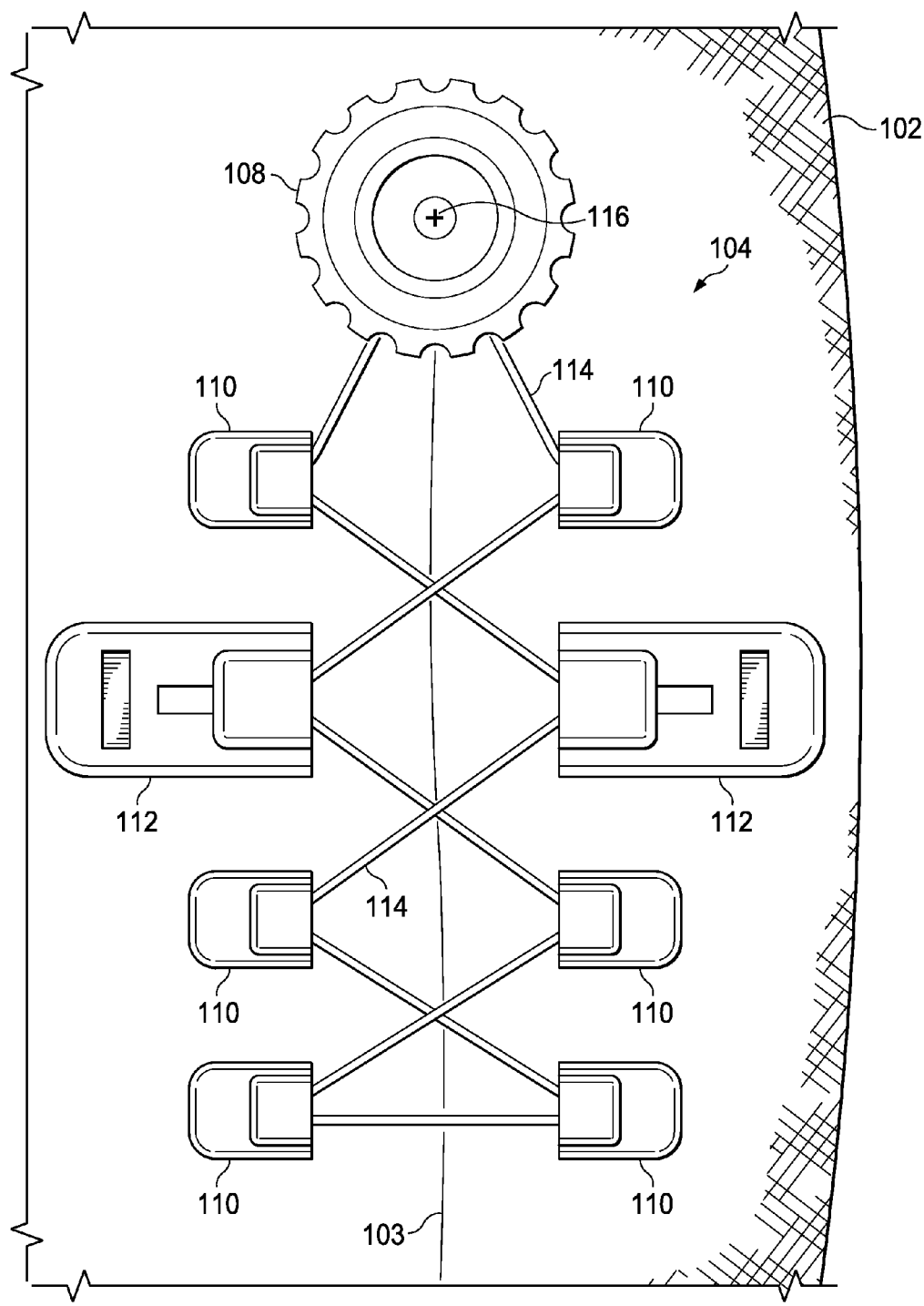
FIG. 2A is a partial front view of the therapy system of FIG. 1, illustrating additional details of an example embodiment of a compression control member.
Figure 2B:
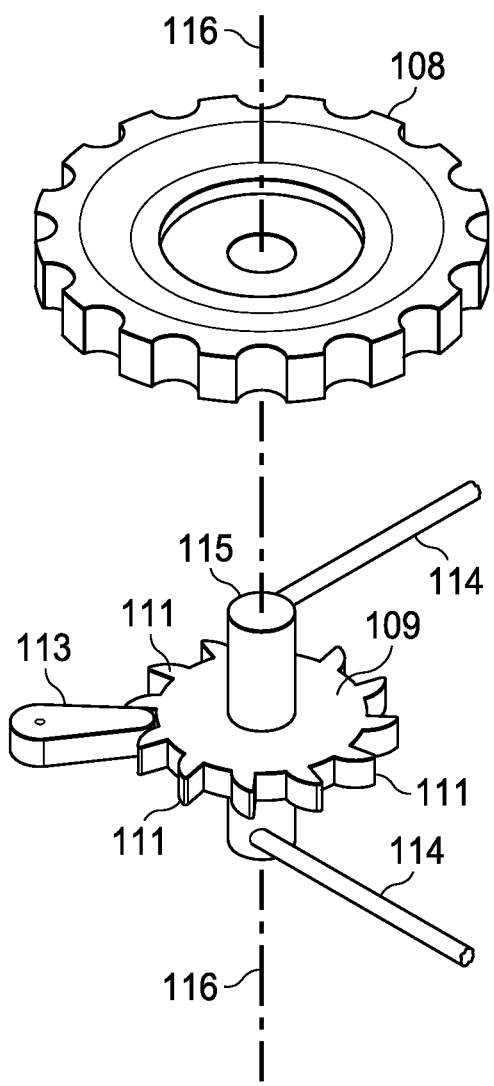
FIG. 2B is an exploded view of an example embodiment of a ratchet assembly that may be associated with the compression control member of FIG. 2A.

FIG. 2A is a detail front view, and FIG. 2B is an exploded view, illustrating additional details that may be associated with exemplary embodiments of the compression control members 104. The illustrative compression control member 104 of FIG. 2A and FIG. 2B is disposed on an upper portion of the trunk 107 of the bandage 102, and may be associated with the compression zone 95. A tensioner 108 may be coupled to the bandage 102 so that the compression line 103 intersects an axis 116 of the tensioner 108. In other exemplary embodiments, the tensioner 108 may be offset from the compression line 103 or may be positioned on other portions of the upper portion of the bandage 102.

The tensioner 108 may be a ratcheting device, such as a dial, having a round gear 109 with teeth 111 and a pawl 113. The gear 109 may be coupled to the tensioner 108 by an axle 115. The axle 115 may be coaxial with the axis 116. The pawl 113 may be a pivoting spring loaded finger, for example, which may also be referred to as a click. In some illustrative embodiments, the pawl 113 may be biased to have an end in contact with the teeth 111 of the gear 109. The gear 109 can be coupled to the tensioner 108 and axially aligned so that rotation of the tensioner 108 causes rotation of the gear 109 in a same direction. The teeth 111 may be asymmetrical, having a moderate slope, such as a gradually increasing slope or curved slope, on a first edge and a steeper slope, such as a perpendicular surface, on a second edge. The pawl 113 can be configured to engage the teeth 111 to allow rotation of the gear 109 in a first direction and prevent rotation of the gear 109 in a second direction, opposite the first direction. For example, in some exemplary embodiments, the tensioner 108 may be rotated clockwise. In response, the gear 109 rotates clockwise, causing the pawl 113 to slide over the moderate slope of each tooth 111 so that the tooth 111 and the gear 109 may advance in a clockwise direction. In these exemplary embodiments, the tensioner 108 may be rotated counterclockwise. In response, the gear 109 rotates counterclockwise, causing the pawl 113 to engage the steep slope of an adjacent tooth 111. When the pawl 113 engages the steep slope, the pawl 113 prevents rotation of the tooth 111 past the pawl 113, preventing rotation of the gear 109, and consequently the tensioner 108, in the counterclockwise direction. Counterclockwise rotation may be achieved, for example, by moving the tensioner 108 and the gear 109 along the axis 116 of the tensioner 108 so that the teeth 111 of the gear 109 and the pawl 113 occupy different planes perpendicular to the axis 116.

The axle 115 may be configured to rotate with the tensioner 108 and further configured to receive at least a portion of a tension member, such as a wire 114. In some exemplary embodiments, the wire 114 may be coupled to the axle 115. If the axle 115 rotates in response to the rotation of the tensioner 108, the wire 114 may wrap around the axle 115. In some embodiments, if the tensioner 108 is rotated clockwise, the wire 114 may wrap around the axle 115, and if the tensioner 108 is rotated counterclockwise, the wire 114 may unwrap from the axle 115.

Referring to FIG. 2A, the compression control member 104 may include six guide members 110 and two indicator guide members 112. In other embodiments, a different number of guide members 110 and indicator guide members 112 may be used. The guide members 110 can be coupled to the bandage 102 on opposing sides of the compression line 103. For example, three guide members 110 may be coupled to a first side of the compression line 103, and three guide members 110 may be coupled to a second side of the compression line 103 so that each guide member 110 is opposite another guide member 110. Similarly, the indicator guide members 112 can be coupled to the bandage 102 on opposing sides of the compression line 103. In some exemplary embodiments having one indicator guide member 112, the indicator guide member 112 may be coupled to the bandage 102 opposite a guide member 110. In other exemplary embodiments having one indicator guide member 112, the indicator guide member 112 may be coupled to the bandage 102 opposite the tensioner 108, for example, if the tensioner 108 is positioned on a side of the compression line 103.

The indicator guide members 112 may provide an indication of an amount of compression applied in the compression zone 95. In some embodiments, the indicator guide members 112 may be positioned adjacent to the compression line 103 proximate to a center of the compression zone 95. In other embodiments, the indicator guide members 112 may be positioned in other portions of the compression zone 95. The guide members 110 may be disposed along a length of the compression line 103 proximate to the indicator guide members 112. In some exemplary embodiments, one pair of guide members 110 may be positioned between the indicator guide members 112 and the tensioner 108, and two pairs of guide members 110 may be placed between the indicator guide members 112 and the adjacent compression control member 104. In some exemplary embodiments, the guide members 110, the indicator guide members 112, and the tensioner 108 may be equidistantly spaced from each other. The guide members 110 and the indicator guide members 112 may be configured to receive at least a portion of the wire 114.

Each guide member 110 and indicator guide member 112 can be coupled to the bandage 102 to distribute a force across a portion of the compression zone 95. For example, the wire 114 may exert a force on each guide member 110 or indicator guide member 112 toward the compression line 103. In some embodiments, the guide members 110 and the indicator guide members 112 may distribute the force across the compression zone 95. In some exemplary embodiments, more guide members 110 and indicator guide members 112 may be positioned on the bandage 102 to further distribute the force applied by the compression control member 104 to the bandage 102. In some embodiments, additional guide members 110 or indicator guide members 112 may be used to increase the size of the compression zone 95.

The wire 114 may have a first end that can be coupled to the tensioner 108 and, in particular, to the axle 115 of the tensioner 108. The wire 114 can be threaded through the guide members 110 and the indicator guide members 112, and a second end of the wire 114 can also be coupled to the tensioner 108. For example, the wire 114 can be threaded using a criss-cross lacing. For example, the wire 114 may be alternatingly passed through the guide members 110 and the indicator guide member 112 on opposing sides of compression line 103, as illustrated in FIG. 2A.

In some exemplary embodiments, the wire 114 may be a single piece of stainless steel material. In other exemplary embodiments, the wire 114 may be woven of stainless steel or may be multiple pieces of stainless steel coupled or joined together. In other exemplary embodiments, the wire 114 may be formed of other materials that are light, strong, resistant to stretching, and have a low coefficient of friction.

If the tensioner 108 is rotated, causing the wire 114 to wrap at least partially around the axle 115, a length of the wire 114 extending between the guide members 110 and the indicator guide members 112 may decrease. Decreasing a length of the wire 114 may cause a force to be exerted on the guide members 110 and the indicator guide members 112 that pulls the guide members 110 and the indicator guide members 112 toward the compression line 103. The force may be transmitted to the trunk 107 and, in response, may decrease the circumference of the bandage 102 proximate to the compression control member 104, applying compression to the leg 106 disposed adjacent the compression zone 95.

Figure 3A:
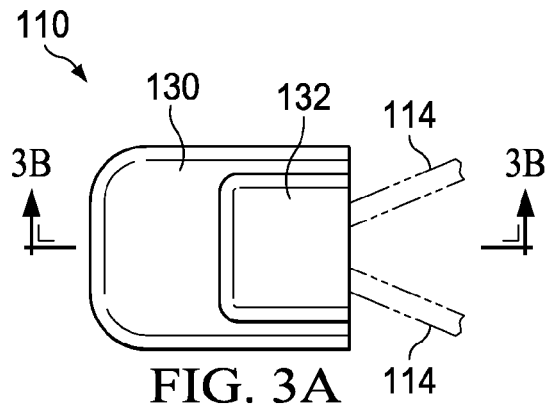
FIG. 3A is a front view of an example embodiment of a guide member that may be associated with the compression control member of FIG. 2A.
Figure 3B:
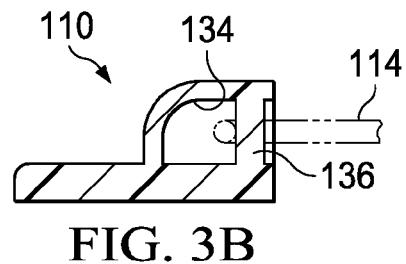
FIG. 3B is a sectional view of the guide member of FIG. 3A taken along line 3B-3B.
Figure 3C:
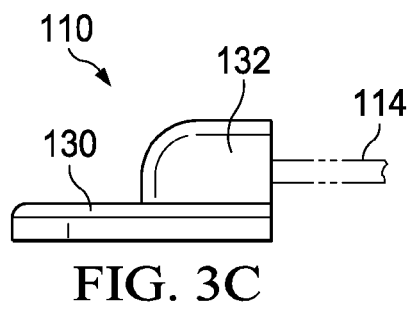
FIG. 3C is a bottom view of the guide member in FIG. 3A.
Figure 3D:
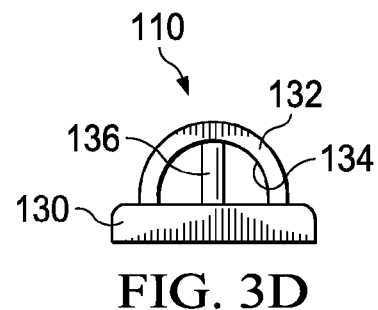
FIG. 3D is a side elevation view of the guide member in FIG. 3A.

FIG. 3A is a front view, illustrating additional details that may be associated with some embodiments of the guide member 110. FIG. 3B is a sectional view, illustrating additional details that may be associated with some embodiments of the guide member 110. FIGS. 3C and 3D are elevation views, illustrating additional details that may be associated with some embodiments of the guide member 110. In some embodiments, the guide member 110 may include a base 130 and a receiver 132. The base 130 may be a rectangular body configured to couple to the bandage 102, for example. In some exemplary embodiments, the base 130 may be a solid body that may be adhesively mounted to the bandage 102. In other exemplary embodiments, the base 130 may be a hollow body that may be sewn, welded, or otherwise coupled to the bandage 102. The base 130 may be formed of a variety of materials for example, plastics, metals, fabrics, and the like.

The receiver 132 may be coupled to a top of the base 130. In some embodiments, the receiver 132 may be positioned on the base 130 so that an end of the receiver 132 is flush with an end of the base 130. The receiver 132 may extend from the end of the base 130 toward an opposite end of the base 130. In some exemplary embodiments, the receiver 132 may extend a portion of a length of the base 130. In other exemplary embodiments, the receiver 132 may be positioned in other locations of base 130 and may have ends coterminous with the base 130. The receiver 132 may extend away from the base 130. In some embodiments, the receiver 132 may have a height from a top of the base 130 to a top of the receiver 132 that is greater than a diameter of the wire 114. The receiver 132 may have a cavity 134 formed between an upper portion of the receiver 132 and the top of the base 130. The cavity 134 can extend into the receiver 132 from the end of the base 130. A post 136 can be disposed within the cavity 134. The post 136 may extend from the upper portion of the receiver 132 to the top of the base 130. The post 136 may be coupled at an upper end of the post 136 to the receiver 132 and at a lower end of the post 136 to the base 130. The post 136 may be disposed proximate to the end of the base 130. In other exemplary embodiments, the post 136 may be disposed in other locations within the cavity 134.

The cavity 134 may have gaps between outer walls of the receiver 132 and the post 136. The gaps may allow the wire 114 to pass between a first side of the post 136 and the wall of the receiver 132, into the cavity 134, and out of the cavity 134 between a second side of the post 136 and another wall of the receiver 132. In some exemplary embodiments, the cavity 134 may be shaped to aid in the assembly of the therapy system 100. For example, a rear portion of the cavity 134 that is opposite the post 136 may be curved so that, if the wire 114 is inserted into the cavity 134, the rear portion may cause the end of the wire 114 to turn in an opposite direction. In some exemplary embodiments, the base 130, the receiver 132, and the post 136 may be a unibody construction. In other exemplary embodiments, the base 130, the receiver 132, and the post 136 may be elements manufactured separately and coupled together in a subsequent assembly process.

Figure 4A:
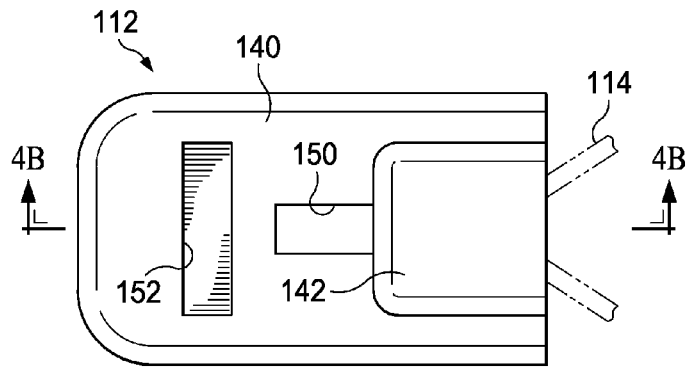
FIG. 4A is a front view of an example embodiment of an indicator guide member that may be associated with the compression control member of FIG. 2A.
Figure 4B:
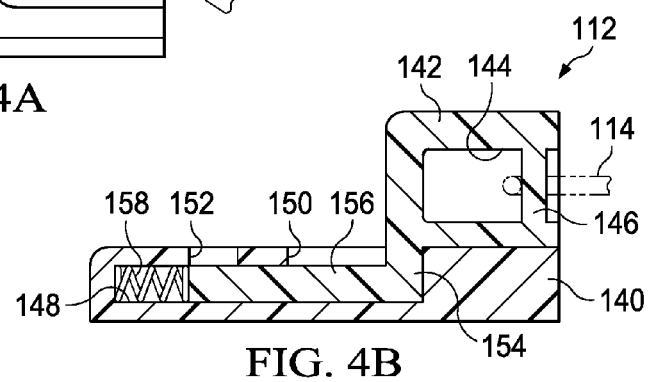
FIG. 4B is a sectional view of the indicator guide member in FIG. 4A taken along line 4B-4B in a first position.
Figure 4C:
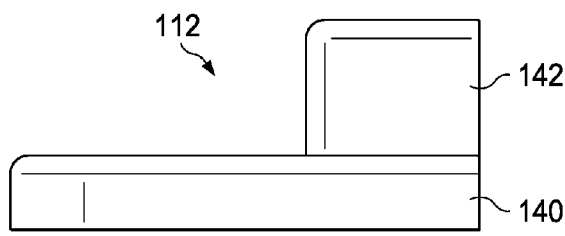
FIG. 4C is a bottom view of the indicator guide member of FIG. 4A.
Figure 4D:
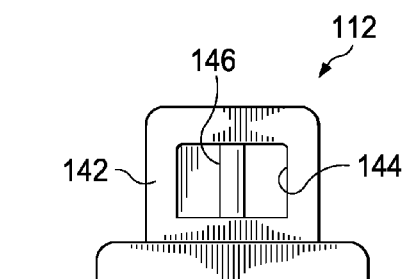
FIG. 4D is a side elevation view of the indicator guide member of FIG. 4A.
Figure 4E:
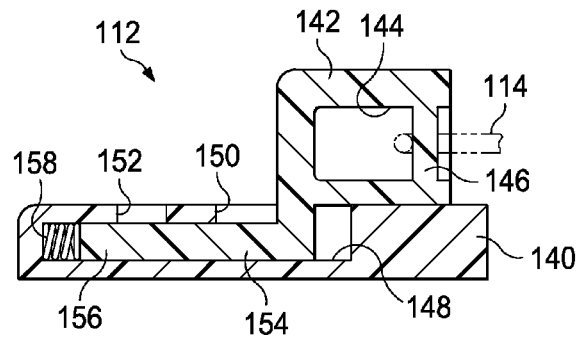
FIG. 4E is a sectional view of the indicator guide member of FIG. 4A taken along line 4B-4B in a second position.

FIG. 4A is a front view, illustrating additional details that may be associated with some embodiments of the indicator guide member 112 of FIG. 2A, FIGS. 4B is a sectional view, illustrating additional details that may be associated with some embodiments of the indicator guide member 112 in a displaced position. FIGS. 4C and 4D are elevation views, illustrating additional details that may be associated with some embodiments of the indicator guide member 112. FIG. 4E is a sectional view, illustrating additional details that may be associated with some embodiments of the indicator guide member 112 in a rest position. In some embodiments, the indicator guide members 112 can provide a visual indication of the compression applied in a particular compression zone. The indicator guide member 112 may include a base 140 and a receiver 142. The base 140 may be a rectangular body configured to be coupled to the bandage 102. In some exemplary embodiments, the base 140 may be a solid body that may be adhesively mounted to the bandage 102. In other exemplary embodiments, the base 140 may be a hollow body that may be sewn, welded, or otherwise coupled to the bandage 102. The base 140 may be formed of a variety of materials such as, plastic, metal, and fabric, for example. The base 140 may further include an indicator cavity 148. In some embodiments, the indicator cavity 148 may be formed in a rearward portion of the base 140 and may include a slot 150 and an indicator window 152. Both the slot 150 and the indicator window 152 may extend through a top wall of the base 140 into the indicator cavity 148, allowing visual access to the indicator cavity 148.

In some embodiments, the receiver 142 may movably mount to a top of the base 140 as described in more detail below. In some exemplary embodiments, the receiver 142 may be positioned on the base 140 so that an end of the receiver 142 may be separated from an end of the base 140. In other exemplary embodiments, the receiver 142 may be positioned in other locations of the base 140. The receiver 142 may extend away from the base 140. In some embodiments, the receiver 142 may have a height that is greater than a diameter of the wire 114. The receiver 142 may have a cavity 144 formed between an upper portion of the receiver 142 and a lower portion of the receiver 142 that is proximate to the base 140. The cavity 144 may extend into the receiver 142 from the end of the receiver 142 proximate to the edge of the base 140. A post 146 can be disposed within the cavity 144 and may extend from the top portion of the cavity 144 to the bottom portion of the cavity 144 that is proximate to the top of the base 140. In some embodiments, the post 146 may be disposed proximate to the end of the receiver 142. In other exemplary embodiments, the post 146 may be disposed in other locations within the cavity 144. The cavity 144 may have gaps between outer walls of the receiver 142 and the post 146. In some embodiments, the gaps may allow the wire 114 to pass between a first side of the post 146 and the wall of the receiver 142, into the cavity 144, and out of the cavity 144 between a second side of the post 146 and another wall of the receiver 142. In some exemplary embodiments, the cavity 144 may be shaped to aid in the assembly of the therapy system 100. For example, a rear portion of the cavity 144 that is opposite the post 146 may be curved so that, if the wire 114 is inserted into the cavity 144, the rear portion may cause the end of the wire 114 to turn in an opposite direction.

In some embodiments, the receiver 142 may include a boss 154 that may extend toward the base 140 from an exterior rear portion of the receiver 142. In some exemplary embodiments, the boss 154 may couple to an opposite end of the receiver 142 from the post 146. The boss 154 can be configured to extend from the receiver 142 through the slot 150 and into the indicator cavity 148. The slot 150 and the boss 154 may have a width that is substantially similar so that the boss 154 may pass through the slot 150 and slide from a first end of the slot 150 to a second end of the slot 150. In some embodiments, a beam 156 may couple to an end of the boss 154 that is opposite the receiver 142 and may extend in a direction away from the receiver 142 into the indicator cavity 148. The beam 156 may have a length so that the beam 156 may extend from the boss 154 to pass under the slot 150 and the indicator window 152 within the indicator cavity 148. The indicator cavity 148 has a length from a first end to a second end that may be greater than the length of the beam 156.

A spring 158 may be mounted in the indicator cavity 148 between an end of the beam 156 and the second end 105 of the indicator cavity 148. In some exemplary embodiments, the spring 158 is at rest in FIG. 4E and displaced in FIG. 4B. The spring 158 may be configured to exert a force on the beam 156 to pull the beam 156 and the coupled receiver 142 toward the second end of the indicator cavity 148. If the wire 114 is inserted into the cavity 144, and the therapy system 100 is placed under compression by the compression control member 104, the receiver 142 and the beam 156 may be pulled away from the second end of the indicator cavity 148, overcoming the spring force of the spring 158. In some exemplary embodiments, the spring 158 may be selected to so that, if the spring 158 is moved from the at rest position of FIG. 4E to the displaced position of FIG. 4B, a therapeutic compression may be applied to the leg 106. A color indicator may be placed on an end of an upper surface of the beam 156 facing the indicator window 152. In some embodiments, if the spring force of the spring 158 is overcome and a therapeutic compression is applied to the leg 106, the beam 156 may move through the indicator cavity 148 below the indicator window 152, and the color indicator may be exposed through the indicator window 152. In other exemplary embodiments, the color indicator may be other types of visual cues. In still other exemplary embodiments, the color indicator and the indicator window 152 may be replaced with a mechanism, such as a strain gauge and an LCD display, that is configured to display the amount of compression applied to the leg 106 based on the displacement of the spring 158.

In operation of the therapy system 100, the bandage 102 may be sized for a limb, such as the leg 106, and may provide the aperture 99 at the first end 101 and the aperture 97 at the second end 105. The leg 106 may be inserted into the aperture 99 of the first end 101 of the bandage 102 so that the foot of the leg 106 is positioned proximate to the second end 105 of the bandage 102 adjacent the third compression zone 91, the ankle of the leg 106 is positioned proximate to the middle portion of the bandage 102 adjacent to the second compression zone 93, and the calf of the leg 106 is positioned proximate to the upper portion of the bandage 102 adjacent to the first compression zone 95. If the bandage 102 is sized and the leg 106 is inserted into the interior of the bandage 102, the interior surface of the bandage 102 may contact the epidermis of the leg 106.

Each compression control member 104 may be individually operated to control compression to the a limb. For example, during use, the trunk 107 of the bandage 102 may cover a portion of the leg 106. Actuation of the compression control members 104 can increase the compressive force applied to the trunk 107 of the bandage 102 at the location of the compression control member 104 so that compression applied to the leg 106 may also be increased.

Each compression control member 104 may be configured to apply compression to a compression zone independently of adjacent compression systems 104. For example, the compression control member 104 located in the third compression zone 91 may apply compression to the foot portion of the leg 106. Compression can be applied to the third compression zone 91 without applying compression to the second compression zone 93 or the first compression zone 95. Similarly, both the compression control member 104 located on the compression zone 93 or the compression control member 104 located on the compression zone 95 may be operated to apply compression to the bandage 102 without requiring operation of the other compression control members 104 located on the bandage 102. Independent operation of the compression control members 104 allows for application of differing amounts of compression to each portion of the bandage 102. Consequently, differing levels of therapeutic compression may be prescribed for the foot, the ankle, and the calf of the leg 106 to create the compression profile.

In some embodiments, to apply a prescribed compression profile, the tensioner 108 of the compression control member 104 located on the compression zone 91 may be rotated in a first direction, for example in a clockwise direction, causing the wire 114 to wrap partially around the axle 115. The rotation may apply compression to the compression zone 91 proximate to the foot of the leg 106. In some embodiments, the rotation of the tensioner 108 of the compression control member 104 of the compression zone 91 may be continued until the indicator guide member 112 indicate that the prescribed compression is applied to the compression zone 91. The tensioners 108 of the compression control member 104 of the compression zone 93 and the compression zone 95 may also be rotated until the respective indicator guide members 112 indicate that the prescribed compression is applied to the compression zone 93 and the compression zone 95.

In other embodiments, rotation of the tensioner 108 of the compression control member 104 of the compression zone 91 may be stopped before the indicator guide members 112 indicate that a prescribed compression has been applied to the leg 106. The tensioner 108 of the compression control member 104 located adjacent to the second compression zone 93 may be rotated in the first direction, causing the wire 114 to wrap partially around the axle 115, applying compression to the compression zone 93 proximate to the ankle of the leg 106. The rotation of the tensioner 108 of the compression control member 104 of the compression zone 93 may be stopped before the indicator guide members 112 indicate that a prescribed compression is being applied to the leg 106. Then, the tensioner 108 of the compression control member 104 located on the compression zone 95 may rotated in the first direction, causing the wire 114 to wrap partially around the axle 115, applying compression to the compression zone 95 proximate to the calf of the leg 106. Again, the rotation of the tensioner 108 of the compression control member 104 of the compression zone 95 may be stopped before the indicator guide members 112 indicate that a prescribed compression is being applied to the leg 106. The tensioner 108 of the compression control member 104 located on the compression zone 91 may be rotated in the first direction, causing the wire 114 to wrap further around the axle 115, applying compression to the compression zone 91 proximate to the foot of the leg 106. Each tensioner 108 may be consecutively rotated to partially apply compression to each compression zone 91, 93, 95 until the indicator guide members 112 of each compression control member 104 provide the visual indication that the prescribed compression is being applied to each compression zone 95, 93, 91.

FIG. 5 is a partial rear view illustrating additional details that may be associated with some embodiments of the bandage 102 of FIG. 1. The bandage 102 may be separated along the length L of the bandage 102 to form panels 118. The panels 118 may have edges 120 on lateral sides of each panel 118. The edges 120 may be parallel to the length L of the bandage 102. The edges 120 of each panel 118 may extend the length L of the bandage 102. A clip mechanism 129 may be coupled to each edge 120 of each panel 118. Each clip mechanism 129 can also extend the length L of the bandage 102. The clip mechanism 129 is operable to engage an adjacent clip mechanism 129 to secure two panels 118 together along adjacent edges 120. In this manner, the bandage 102 may be assembled by coupling a plurality of panels 118 together to form the bandage 102 having a tubular shape and an interior into which the leg 106 may be inserted as shown in FIG. 1. At least one of the panels 118 may include the compression control members 104. In some exemplary embodiments, each panel 118 may include the compression control members 104.

In some embodiments, adjacent panels 118 may be joined by an extender 122. The extender 122 may have a first edge that couples to the edge 120 of a first panel 118 and a second edge that couples to the edge 120 of a second panel 118. In some exemplary embodiments, the extender 122 may couple to the edge 120 so that the clip mechanism 129 overlays to the extender 122. The extender 122 may have a width perpendicular to the edge 120. In some exemplary embodiments, if the extender 122 is taut, opposing clip mechanisms 129 may not engage. If opposing clip mechanisms 129 of two adjacent panels 118 joined by an extender 122 are engaged, the extender 122 may be compressed so that the width of the extender 122 decreases. In this manner, the circumference of the bandage 102 may be increased or decreased as necessary while maintaining the bandage 102 as a unitary body. The extenders 122 may be formed of the same material as the bandage 102. In some exemplary embodiments, the extenders 122 may be formed of an elastic material.

Figure 6B:
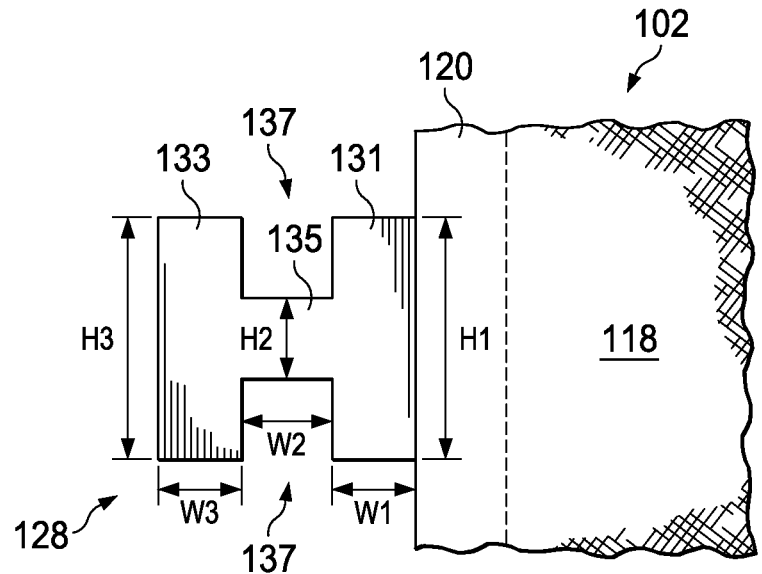
FIG. 6B is a detail view of a fastener of one of the clip mechanisms in FIG. 5.

FIGS. 6A is an elevation view, illustrating additional details that may be associated with some embodiments of a portion of opposing clip mechanisms 129 in a disengaged position. Each clip mechanism 129 may include a plurality of fasteners 128. FIG. 6B is a detail view, illustrating additional details that may be associated with some embodiments of a fastener 128. In some embodiments, each fastener 128 may have a substantially I or H shape and may be coupled to the edge 120 of the panel 118 of the bandage 102. Each fastener 128 may include a base leg 131, a distal leg 133, and a connecting leg 135. The base leg 131 may be coupled to the edge 120, for example, by adhesion, welding, or fasteners, for example. In some exemplary embodiments, the base leg 131 may be a rectangular body having a width W1 extending away from the edge 120 and a height H1 parallel to the edge 120. The connecting leg 135 may be coupled to the base leg 131 proximate to a middle portion of the base leg 131 opposite the edge 120. The connecting leg 135 may have a width W2 and a height H2. In some exemplary embodiments, the width W2 and the height H2 may be substantially the same. In other exemplary embodiments, the width W2 and the height H2 may be different. The distal leg 133 may be a rectangular body having a width W3 parallel to the width W1 of the base leg 131, and a height H3 parallel to the height H1 of the base leg 131. The distal leg 133 may be coupled to the connecting leg 135 proximate to a middle portion of the height H2 of the distal leg 133 opposite the base leg 131.

In some exemplary embodiments, the width W1, the width W2, and the width W3 are substantially the same. In other exemplary embodiments, the width W1, the width W2, and the width W3 are different. The height H1 and the height H3 may be substantially the same, and the height H2 may be less than the height H1 and the height H3 so that gaps 137 may be formed between the base leg 131 and the distal leg 133 adjacent to the connecting leg 135. Each gap 137 may have a size and shape to receive a portion of the distal leg 133 of another fastener 128. In some exemplary embodiments, the size and shape of each gap 137 may substantially match the size and shape of a portion of the distal leg 133 extending from the union of the distal leg 133 and the connecting leg 135 to an end of the distal leg 133 opposite the connecting leg 135. In some exemplary embodiments, each fastener 128 may be configured to receive a portion of the distal leg 133 of another fastener 128, securing opposing fasteners 128 of opposing clip mechanisms 129. The fasteners 128 may be formed of a material having a strength sufficient to resist deformation or failure during the application of compression therapy. For example, the fasteners 128 may be formed of a hard plastic or metal material.

In operation, two adjacent panels 118 may have a pair of opposing clip mechanisms 129. As shown in FIG. 6A, a first clip mechanism 124 may be coupled to a first panel 118, and second clip mechanism 126 may be coupled to a second panel 118. The first clip mechanism 124 and the second clip mechanism 126 may be offset from one another so that a connecting leg 135 of a fastener 128 of the first clip mechanism 124 is offset from a connecting leg 135 of a fastener 128 of the second slip mechanism 126. In the exemplary embodiments, each fastener 128 of the first clip mechanism 124 and the second clip mechanism 126 may be separated from adjacent fasteners 128 by a distance approximately equal to the height H2 of the connecting leg 135.

Figure 7:
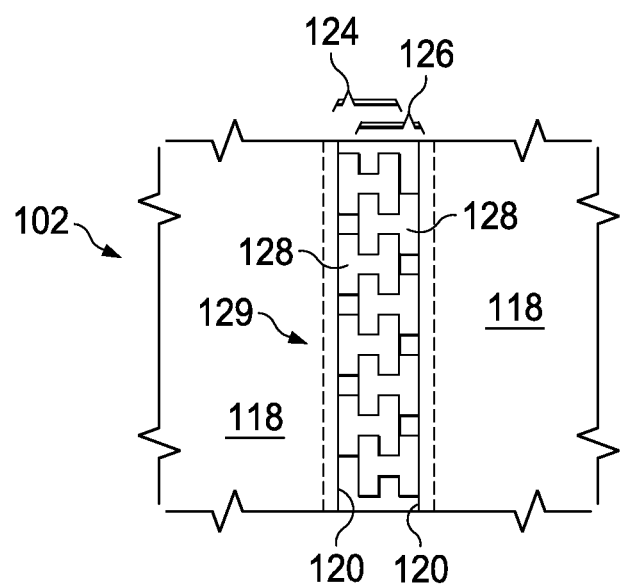
FIG. 7 is a detail view of the clip mechanisms of FIG. 5 in a fastened configuration.

FIG. 7 is an elevation view, illustrating additional details that may be associated with some embodiments of a portion of the opposing clip mechanisms 129 of FIG. 6A in an engaged position. The first clip mechanism 124 and the second clip mechanism 126 may be brought adjacent to each other so that the first clip mechanism 124 and the second clip mechanism 126 may at least partially overlap. In the exemplary embodiment, the distal leg 133 of each fastener of the first clip mechanism 124 may be aligned with the connecting leg 135 of the second clip mechanism 126 and vice versa. The portion of the distal leg 133 extending from the union of the distal leg 133 and the connecting leg 135 of each fastener 128 of the first clip mechanism 124 may be inserted into a gap 137 of a proximate fastener 128 of the second clip mechanism 126. In this manner the first clip mechanism 124 may be engaged to the second clip mechanism 126.

In some exemplary embodiments including the extenders 122, securing the first clip mechanism 124 to the second clip mechanism 126 decreases a circumference of the bandage 102 by a portion of the width of the extender 122, allowing the bandage 102 to be sized to a smaller leg 106. Similarly, the first clip mechanism 124 and the second clip mechanism 126 may be unfastened to allow the bandage 102 to be sized to a larger leg 106. Still further, two panels 118 unattached by an extender 122 may be joined by engaging the first clip mechanism 124 of a first panel 118 to the second clip mechanism 126 of a second panel 118 to complete the circumference of the bandage 102.

With a compression control member incorporated into a bandage, the user, for example, a clinician or a patient, may be able to apply compression with greater adjustability over the compression profile of the leg. The increased adjustability may make application of compression therapy easier compared to conventional compression bandaging. In addition, incorporating the compression control member into the bandage may allow the patient to increase or decrease the amount of compression applied by the bandage to avoid patient discomfort. A bandage may provide localized control of compression at multiple locations of the bandage, allowing adjustment of the compression profile to provide optimum compression therapy to address vascular problems. In addition, increased ease of use provided by the compression control member may increase patient compliance with compression therapy. The clip mechanisms provide a bandage that may sized to the particular leg, allowing for more comfortable application of compression therapy. The bandage may also be less bulky than the traditional compression bandage. A bandage having a compression control member may allow clinicians to apply compression more consistently, increasing the likelihood that compression therapy may be comfortably applied to the patient. Still further, a bandage having a compression control member may permit a patient to remove the bandage and, subsequently, reapply the bandage at the appropriate therapeutic compression without requiring consultation with a clinician.

The systems and methods described herein may provide significant advantages, some of which have already been mentioned. For example, the systems and methods may provide for application of compression therapy appropriate for addressing vascular disease. In addition, the systems and methods may provide higher levels of repeatability of compression therapy compared to conventional systems. In addition, the systems and methods may provide easy access and quick adjustment of the compression provided to the tissue site. Still further, the systems and methods may provide a reduction in bulkiness compared to conventional compression bandages, allowing improved patient comfort and increased patient compliance with compression therapy.

Although certain illustrative, non-limiting exemplary embodiments have been presented, it should be understood that various changes, substitutions, permutations, and alterations can be made without departing from the scope of the appended claims. It will be appreciated that any feature that is described in connection to any one exemplary embodiment may also be applicable to any other exemplary embodiment.

It will be understood that the benefits and advantages described above may relate to one exemplary embodiment or may relate to several exemplary embodiments. It will further be understood that reference to "an" item refers to one or more of those items.

The steps of the methods described herein may be carried out in any suitable order, or simultaneously where appropriate.

Where appropriate, features of any of the exemplary embodiments described above may be combined with features of any of the other exemplary embodiments described to form further examples having comparable or different properties and addressing the same or different problems.

It will be understood that the above description of preferred exemplary embodiments is given by way of example only and that various modifications may be made by those skilled in the art. The above specification, examples and data provide a complete description of the structure and use of exemplary embodiments of the invention. Although various exemplary embodiments of the invention have been described above with a certain degree of particularity, or with reference to one or more individual exemplary embodiments, those skilled in the art could make numerous alterations to the disclosed exemplary embodiments without departing from the scope of the claims.

We claim:

1. A compression therapy apparatus, comprising:
   an elastic bandage comprising a trunk, a first end, a second end, and a compression line between the first end and the second end, the trunk having a leg portion, an ankle portion, and a foot portion; and
   a plurality of compression control members disposed on the trunk along the compression line, a first of the compression control members being disposed on the leg portion, a second of the compression control members being disposed on the ankle portion, and a third of the compression control members being disposed on the foot portion;
   wherein each compression control member defines a compression zone and is adapted to independently control a therapeutic compression associated with the compression zone; and
   wherein the plurality of compression control members are configured to provide a substantially continuous compression profile along the compression line;
   wherein each compression control member comprises a tension member and a tensioner;

wherein the tension member is laced over the compression line and coupled to the tensioner; and wherein the tensioner is operable to change tension in the tension member to control the therapeutic compression.

2. The compression therapy apparatus of claim 1, wherein the plurality of compression control members are contiguously disposed on the trunk.

3. The compression therapy apparatus of claim 1, wherein the bandage is formed of neoprene.

4. The compression therapy apparatus of claim 1, wherein the first end comprises an aperture adapted to receive a limb, and the bandage is adapted to cover the limb.

5. The compression therapy apparatus of claim 1, wherein the tension member is formed of steel.

6. The compression therapy apparatus of claim 1, further comprising at least two clip mechanisms coupled to the trunk and configured to adjust a circumference size of the bandage.

7. The compression therapy apparatus of claim 1, wherein each compression control member comprises an indicator guide member.

8. The compression therapy apparatus of claim 1, wherein each compression control member comprises an indicator guide member operatively coupled to the tension member.

9. The compression therapy apparatus of claim 1, wherein the compression zone extends circumferentially around the bandage.

10. A compression therapy apparatus comprising:
a bandage having a first end, a second end, a trunk extending from the first end to the second end, and opposing edges extending from the first end to the second end; at least one pair of opposing clip mechanisms coupled to the bandage adjacent the opposing edges along the trunk of the bandage and operable to adjust the circumference of the bandage; and
three compression control members coupled to the bandage and configured to exert a force on the bandage to provide therapeutic compression to the trunk in a compression zone, a first compression control member coupled to a first compression zone, a second compression control member coupled to a second compression zone, and a third compression control member coupled to a third compression zone, wherein the compression control members comprise: a tensioner having an axle and a gear having teeth configured to engage a pawl mounted to the bandage;
a plurality of guide members coupled to the bandage; and
a tension member coupled to the axle of the tensioner and each guide member, the tension member configured to exert a force on the guide members causing compression of the bandage.

11. The apparatus of claim 10, wherein:
each compression control member is configured to exert an independent therapeutic compression to a respective compression zone.

12. The apparatus of claim 10,
wherein the compression control member further comprises at least one indicator guide member coupled to the bandage and configured to indicate a compressive load applied by the bandage.

13. The apparatus of claim 10,
wherein the plurality of guide members have a base portion configured to couple to the bandage and a receiving portion having a cavity and a post; and
wherein the tension member is configured to engage the post to exert the force on the guide members causing compression of the bandage.

14. The apparatus of claim 10,
wherein the compression control member further comprises at least one indicator guide member coupled to the bandage and configured to indicate a compressive load applied by the bandage; the indicator guide member comprising:
a base portion having an indicator cavity having a first end and a second end, a slot extending from a top portion of the base portion into the indicator cavity, and an indicator window positioned adjacent to the slot and extending from the top portion of the base portion into the indicator cavity,
a spring positioned in the indicator cavity, and
a receiving portion having a cavity and a post, the post disposed within the cavity and adapted to receive the tension member, the receiving portion further including a boss extending from a lower portion of the receiving portion parallel to the post, and a beam coupled to the boss and extending away from the receiving portion perpendicular to the boss, the boss and the beam disposed within the indicator cavity and an end of the beam configured to engage the spring;
wherein when the tension member exerts the force on the guide members, the spring is displaced in response to a therapeutic amount of compression to expose an indicator mounted to the beam in the indicator window.

15. The apparatus of claim 10, wherein the compression control member further comprises:
a plurality of guide members having a base portion configured to couple to the bandage and a receiving portion having a cavity and a post, coupled to the bandage;
at least one indicator guide member coupled to the bandage and configured to indicate a compressive load applied by the bandage, the indicator guide member comprising:
a base portion having an indicator cavity having a first end and a second end, a slot extending from a top portion of the base portion into the indicator cavity, and an indicator window positioned adjacent to the slot and extending from the top portion of the base portion into the indicator cavity,
a spring positioned in the indicator cavity, and
a receiving portion having a cavity and a post, the post disposed within the cavity and adapted to receive the tension member, the receiving portion further including a boss extending from a lower portion of the receiving portion parallel to the post, and a beam coupled to the boss and extending away from the receiving portion perpendicular to the boss, the boss and the beam disposed within the indicator cavity and an end of the beam configured to engage the spring;
wherein when the tension member exerts the force on the guide members, the spring is displaced in response to a therapeutic amount of compression to expose an indicator mounted to the beam in the indicator window.

16. The apparatus of claim 10, wherein the pair of opposing clip mechanisms comprise:
a first clip mechanism having a plurality of fasteners coupled to a first edge of opposing edges of the bandage; and
a second clip mechanism having a plurality of fasteners coupled to a second edge of opposing edges of the bandage;

wherein the first clip mechanism is configured to engage the second clip mechanism to couple the first edge to the second edge along the trunk.

17. The apparatus of claim 10, wherein the clip mechanisms comprise:
   a first clip mechanism having a plurality of fasteners coupled to a first edge of opposing edges of the bandage;
   a second clip mechanism having a plurality of fasteners coupled to a second edge of opposing edges of the bandage; and
   each fastener of the first clip mechanism and the second clip mechanism has a base portion, a connecting portion, and a distal portion, the base portion coupled to the edge, the connecting portion extending between the base portion and the distal portion and having a size less than the distal portion and the base portion to form a gap to receive a portion of a distal portion of a fastener of the opposing clip mechanism;
   wherein the first clip mechanism is configured to engage the second clip mechanism to couple the first edge to the second edge along the trunk.

18. The apparatus of claim 10, wherein the bandage comprises a plurality of panels releasably coupled by the pair of opposing clip mechanisms.

19. The apparatus of claim 10, wherein the bandage comprises a plurality of panels releasably coupled by the pair of opposing clip mechanisms, each panel further coupled to an adjacent panel by an extender so that when the opposing clip mechanisms are disengaged, the panels are separated by a width of the extender and when the opposing clip mechanisms are engaged, the width of the extender is decreased.

20. The apparatus of claim 10, wherein the bandage is formed of neoprene.

21. The apparatus of claim 10, wherein the bandage comprises a plurality of panels releasably coupled by the pair of opposing clip mechanisms, each panel further coupled to an adjacent panel by an extender so that when the opposing clip mechanisms are disengaged, the panels are separated by a width of the extender and when the opposing clip mechanisms are engaged, the width of the extender is decreased, and wherein each panel and each extender is formed of neoprene.

22. A method for providing compression therapy to a tissue site, the method comprising:
   providing a compression therapy apparatus comprising:
   an elastic bandage comprising a trunk, a first end, a second end, and a compression line between the first end and the second end, the trunk having a leg portion, an ankle portion, and a foot portion;
   a plurality of compression control members disposed on the trunk along the compression line, a first of the compression control members being disposed on the leg portion, a second of the compression control members being disposed on the ankle portion, and a third of the compression control members being disposed on the foot portion; wherein each compression control member defines a compression zone and is adapted to independently control a therapeutic compression associated with the compression zone;
   wherein the plurality of compression control members are configured to provide a substantially continuous compression profile along the compression line; wherein each compression control member comprises a tension member and a tensioner;
   wherein the tension member is laced over the compression line and coupled to the tensioner; and
   wherein the tensioner is operable to change tension in the tension member to control the therapeutic compression:
   determining a size of the tissue site; sizing the bandage to accommodate the tissue site; inserting the tissue site into an aperture of the bandage; and operating the compression control member to apply therapeutic compression.

23. The method of claim 22, wherein operating the compression control member to apply therapeutic compression comprises:
   operating the first compression control member to apply compression to the leg portion;
   operating the second compression control member to apply compression to the ankle portion; and
   operating the third compression control member to apply compression to the foot portion.

24. The method of claim 22, wherein operating the compression control member to apply therapeutic compression comprises:
   operating the first compression control member to apply compression to the leg portion;
   operating the second compression control member to apply compression to the ankle portion; and
   operating the third compression control member to apply compression to the foot portion;
   determining whether therapeutic compression is applied to the tissue site; and
   if therapeutic compression is not being applied to the tissue site repeating operation of the first compression control member, the second compression control member, and the third compression control member until therapeutic compression is applied.

25. The method of claim 22, wherein sizing the bandage comprises operating the clip mechanisms to adjust the size of the bandage to accommodate the tissue site by engaging a first plurality of fasteners of a first clip mechanism to a second plurality of fasteners of a second clip mechanism to decrease the size of the bandage.

26. The method of claim 22, wherein sizing the bandage comprises operating the clip mechanisms to adjust the size of the bandage to accommodate the tissue site by disengaging a first plurality of fasteners of a first clip mechanism to a second plurality of fasteners of a second clip mechanism to increase the size of the bandage.

27. A method of manufacturing a bandage comprising:
   providing an elastic bandage having a trunk, a first end, a second end, and a compression line between the first end and the second end, the trunk having a leg portion, an ankle portion, and a foot portion; and
   coupling a plurality of compression control members on the trunk along the compression line, a first of the compression control members is disposed on the leg portion, a second of the compression control members is disposed on the ankle portion, and a third of the compression control members is disposed on the foot portion;
   wherein each compression control member defines a compression zone and is adapted to independently control a therapeutic compression associated with the compression zone;
   wherein the plurality of compression control members are configured to provide a substantially continuous compression profile along the compression line;
   wherein each compression control member comprises a tension member and a tensioner;

wherein the tension member is laced over the compression line and coupled to the tensioner; and wherein the tensioner is operable to change tension in the tension member to control the therapeutic compression.

28. The method of claim 27, further comprising coupling a pair of opposing clip mechanisms to the trunk of the bandage proximate to opposing edges of the bandage, the clip mechanism extending from the first end to the second end.

29. A compression therapy apparatus comprising:

a bandage having a first end, a second end, a trunk extending from the first end to the second end, and opposing edges extending from the first end to the second end;

at least one pair of opposing clip mechanisms coupled to the bandage adjacent the opposing edges along the trunk of the bandage and operable to adjust the circumference of the bandage; and three compression control members coupled to the bandage and configured to exert a force on the bandage to provide therapeutic compression to the trunk in a compression zone, a first compression control member coupled to a first compression zone, a second compression control member coupled to a second compression zone, and a third compression control member coupled to a third compression zone, wherein the clip mechanisms comprise: a first clip mechanism having a plurality of fasteners coupled to a first edge of opposing edges of the bandage;

a second clip mechanism having a plurality of fasteners coupled to a second edge of opposing edges of the bandage; and each fastener of the first clip mechanism and the second clip mechanism has a base portion, a connecting portion, and a distal portion, the base portion coupled to the edge, the connecting portion extending between the base portion and the distal portion and having a size less than the distal portion and the base portion to form a gap to receive a portion of a distal portion of a fastener of the opposing clip mechanism;

wherein the first clip mechanism is configured to engage the second clip mechanism to couple the first edge to the second edge along the trunk.

* * * * *